(12) United States Patent
Wang et al.

(10) Patent No.: US 10,980,423 B2
(45) Date of Patent: Apr. 20, 2021

(54) DEVICES AND METHODS FOR PREDICTING HEMOGLOBIN LEVELS USING ELECTRONIC DEVICES SUCH AS MOBILE PHONES

(71) Applicant: University of Washington, Seattle, WA (US)

(72) Inventors: Edward J. Wang, Seattle, WA (US); Shwetak N. Patel, Seattle, WA (US)

(73) Assignee: University of Washington, Seattle, WA (US)

( * ) Notice: Subject to any disclaimer, the term of this patent is extended or adjusted under 35 U.S.C. 154(b) by 234 days.

(21) Appl. No.: 16/060,865

(22) PCT Filed: Dec. 21, 2016

(86) PCT No.: PCT/US2016/067988
§ 371 (c)(1),
(2) Date: Jun. 8, 2018

(87) PCT Pub. No.: WO2017/112753
PCT Pub. Date: Jun. 29, 2017

(65) Prior Publication Data
US 2019/0008392 A1    Jan. 10, 2019

Related U.S. Application Data

(60) Provisional application No. 62/271,222, filed on Dec. 22, 2015, provisional application No. 62/330,968, filed on May 3, 2016.

(51) Int. Cl.
*A61B 5/00*    (2006.01)
*A61B 5/145*    (2006.01)
(Continued)

(52) U.S. Cl.
CPC .............. *A61B 5/0082* (2013.01); *A61B 5/00* (2013.01); *A61B 5/024* (2013.01); *A61B 5/08* (2013.01);
(Continued)

(58) Field of Classification Search
None
See application file for complete search history.

(56) References Cited

U.S. PATENT DOCUMENTS

| | | |
|---|---|---|
| 5,919,134 A | 7/1999 | Diab |
| 6,002,952 A | 12/1999 | Diab et al. |

(Continued)

FOREIGN PATENT DOCUMENTS

| | | |
|---|---|---|
| WO | 2011106792 A2 | 9/2011 |
| WO | 2017112753 A1 | 6/2017 |

OTHER PUBLICATIONS

Anemia Screening, HemoCue America, 2019, 3 pages.
(Continued)

*Primary Examiner* — Neil N Turk
(74) *Attorney, Agent, or Firm* — Dorsey & Whitney LLP

(57) ABSTRACT

Examples described herein include electronic devices which may serve as hemochromatic analyzers, leveraging sensors and computation available on the electronic devices themselves, such as smartphones and smartwatches. In this manner, minor to no hardware modification may be required to a mobile phone or other electronic device to allow the device to predict hemoglobin levels.

12 Claims, 5 Drawing Sheets

(51) Int. Cl.
*A61B 5/1455* (2006.01)
*A61B 5/024* (2006.01)
*A61B 5/08* (2006.01)
*G01N 21/31* (2006.01)

(52) U.S. Cl.
CPC ............ *A61B 5/145* (2013.01); *A61B 5/1455* (2013.01); *A61B 5/14551* (2013.01); *A61B 5/6897* (2013.01); *A61B 5/6898* (2013.01); *A61B 5/0077* (2013.01)

(56) References Cited

U.S. PATENT DOCUMENTS

| | | | |
|---|---|---|---|
| 6,067,462 A | 5/2000 | Diab et al. | |
| 6,229,856 B1 | 5/2001 | Diab et al. | |
| 6,260,577 B1 | 7/2001 | Keller | |
| 6,360,114 B1 | 3/2002 | Diab et al. | |
| 6,388,240 B2 | 5/2002 | Schulz et al. | |
| 6,415,236 B2 | 7/2002 | Kobayashi et al. | |
| 6,430,525 B1 | 8/2002 | Weber et al. | |
| 6,463,311 B1 | 10/2002 | Diab | |
| 6,515,273 B2 | 2/2003 | Al-Ali | |
| 6,606,511 B1 | 8/2003 | Ali et al. | |
| 6,643,530 B2 | 11/2003 | Diab et al. | |
| 6,654,624 B2 | 11/2003 | Diab et al. | |
| 6,684,090 B2 | 1/2004 | Ali et al. | |
| 6,699,194 B1 | 3/2004 | Diab et al. | |
| 6,816,741 B2 | 11/2004 | Diab | |
| 6,822,564 B2 | 11/2004 | Al-Ali | |
| 6,850,787 B2 | 2/2005 | Weber et al. | |
| 6,861,639 B2 | 3/2005 | Al-Ali | |
| 6,961,598 B2 | 11/2005 | Diab | |
| 6,979,812 B2 | 12/2005 | Al-Ali | |
| 6,999,904 B2 | 2/2006 | Weber et al. | |
| 7,003,339 B2 | 2/2006 | Diab et al. | |
| 7,044,918 B2 | 5/2006 | Diab | |
| 7,186,966 B2 | 3/2007 | Al-Ali | |
| 7,215,986 B2 | 5/2007 | Diab et al. | |
| 7,221,971 B2 | 5/2007 | Diab et al. | |
| 7,254,433 B2 | 8/2007 | Diab et al. | |
| 7,295,866 B2 | 11/2007 | Al-Ali | |
| 7,355,512 B1 | 4/2008 | Al-Ali | |
| 7,373,194 B2 | 5/2008 | Weber et al. | |
| 7,377,899 B2 | 5/2008 | Weber et al. | |
| 7,438,683 B2 | 10/2008 | Al-Ali et al. | |
| 7,467,002 B2 | 12/2008 | Weber et al. | |
| 7,471,969 B2 | 12/2008 | Diab et al. | |
| 7,489,958 B2 | 2/2009 | Diab et al. | |
| 7,496,393 B2 | 2/2009 | Diab et al. | |
| 7,499,741 B2 | 3/2009 | Diab et al. | |
| 7,499,835 B2 | 3/2009 | Weber et al. | |
| 7,530,955 B2 | 5/2009 | Diab et al. | |
| 7,596,398 B2 | 9/2009 | Al-Ali et al. | |
| D606,659 S | 12/2009 | Kiani et al. | |
| D621,516 S | 8/2010 | Kiani et al. | |
| 7,865,222 B2 | 1/2011 | Weber et al. | |
| 7,873,497 B2 | 1/2011 | Weber et al. | |
| 7,880,606 B2 | 2/2011 | Al-Ali | |
| 7,988,637 B2 | 8/2011 | Diab | |
| 7,990,382 B2 | 8/2011 | Kiani | |
| 8,036,728 B2 | 10/2011 | Diab et al. | |
| 8,046,040 B2 | 10/2011 | Ali et al. | |
| 8,046,041 B2 | 10/2011 | Diab et al. | |
| 8,046,042 B2 | 10/2011 | Diab et al. | |
| 8,128,572 B2 | 3/2012 | D1ab et al. | |
| 8,150,487 B2 | 4/2012 | Diab et al. | |
| 8,180,420 B2 | 5/2012 | Diab et al. | |
| 8,185,180 B2 | 5/2012 | Diab et al. | |
| 8,190,227 B2 | 5/2012 | Diab et al. | |
| 8,203,438 B2 | 6/2012 | Kiani et al. | |
| 8,224,411 B2 | 7/2012 | Al-Ali et al. | |
| 8,260,577 B2 | 9/2012 | Weber et al. | |
| 8,265,723 B1 | 9/2012 | McHale et al. | |
| 8,280,473 B2 | 10/2012 | Al-Ali | |
| 8,337,403 B2 | 12/2012 | Al-Ali et al. | |
| 8,353,842 B2 | 1/2013 | Al-Ali et al. | |
| 8,471,713 B2 | 1/2013 | Poeze et al. | |
| 8,414,499 B2 | 4/2013 | Al-Ali et al. | |
| 8,437,825 B2 | 5/2013 | Dalvi et al. | |
| 8,457,703 B2 | 6/2013 | Al-Ali | |
| 8,483,787 B2 | 7/2013 | Al-Ali et al. | |
| 8,489,364 B2 | 7/2013 | Weber et al. | |
| 8,498,684 B2 | 7/2013 | Weber et al. | |
| 8,503,712 B2 * | 8/2013 | Ahmed | G06T 7/0014 382/100 |
| 8,532,728 B2 | 9/2013 | Diab et al. | |
| 8,560,032 B2 | 10/2013 | Al-Ali et al. | |
| 8,570,167 B2 | 10/2013 | Al-Ali | |
| 8,570,503 B2 | 10/2013 | Vo et al. | |
| 8,577,431 B2 | 11/2013 | Lamego et al. | |
| 8,630,691 B2 | 1/2014 | Lamego et al. | |
| 8,652,060 B2 | 2/2014 | Al-Ali | |
| 8,676,236 B1 | 3/2014 | Weber et al. | |
| 8,688,183 B2 | 4/2014 | Bruinsma et al. | |
| 8,718,735 B2 | 5/2014 | Lamego et al. | |
| 8,718,737 B2 | 5/2014 | Diab et al. | |
| 8,754,776 B2 | 6/2014 | Poeze et al. | |
| 8,847,740 B2 | 9/2014 | Kiani et al. | |
| 8,802,180 B2 | 11/2014 | Weber et al. | |
| 8,909,310 B2 | 12/2014 | Lamego et al. | |
| 8,929,964 B2 | 1/2015 | Al-Ali et al. | |
| 9,131,883 B2 | 9/2015 | Al-Ali | |
| 9,186,102 B2 | 11/2015 | Bruinsma et al. | |
| 2007/0015981 A1 | 1/2007 | Benaron et al. | |
| 2007/0024949 A1 * | 2/2007 | Kim | G02F 1/2255 359/276 |
| 2010/0099964 A1 | 4/2010 | Oreilly et al. | |
| 2011/0054714 A1 | 3/2011 | Santos et al. | |
| 2012/0277559 A1 * | 11/2012 | Kohl-Bareis | A61B 5/0261 600/324 |
| 2013/0137961 A1 | 5/2013 | Barnes et al. | |
| 2013/0324815 A1 | 12/2013 | Jian et al. | |
| 2014/0243648 A1 | 8/2014 | Dubielczyk | |
| 2015/0148624 A1 | 5/2015 | Benaron | |
| 2015/0305658 A1 | 10/2015 | Islam | |

OTHER PUBLICATIONS

Pronto Pulse Co-Oximeter, Masimo Pronto, 2019, 8 pages.
Wireless Blood Pressure Wrist Monitor, https://ihealthlabs.com/blood-pressure-monitors/wireless-blood-pressure-wrist-monitor/, Jan. 2016, 4 pages.
Wireless Smart Gluco-Monitoring System, iHealth Labs, 2018, 17 pages.
Abdallah, et al., Concentrations of Hemoglobin Fractions Calculation Using Modified Lambert-Beer Law and Solving of an ILL-Posed System of Equations, SPIE., vol. 7715, May 2010, p. 1-9.
Alam, Fuzzy Logic Hemoglobin Sensors, Karlsruhe Institute of Technology, Oct. 5, 2011, 146 pages.
Aziz, et al., A Near Infrared Instrument to Monitor Relative Hemoglobin Concentrations of Human Bone Tissue In Vitro and In Vivo, Review of Scientific Instruments, Apr. 2010, 8 pages.
Brown, et al., Normal Variations in Blood Haemoglobin Concentration, The Journal of Physiology, vol. 104, Apr. 1946, p. 404-407.
Bunn, , Pathogenesis and Treatment of Sickle Cell Disease, The New England Journal of Medicine, vol. 337, No. 11, Sep. 1997, p. 762-769.
De Greef, et al., Bilicam: Using Mobile Phones to Monitor Newborn Jaundice, Proceedings of the 2014 ACM International Joint Conference on Pervasive and Ubiquitous Computing—UbiComp '14 Adjunct, Sep. 2014, p. 331-342.
Fan, et al,, Land Use and Land Cover Change in Guangzhou, China, From 1998 to 2003, Based on Landsat TM/ETM+ Imagery, Sensors, Jul. 2007, p. 1323-1342.
Gehring, et al., Accuracy of Point-of-Care-Testing (POCT) for Determining Hemoglobin Concentrations, Acta anaesthesiologica Scandinavica, Mar. 2002, p. 980-986.
George-Gay, et al., Understanding the Complete Blood Count With Differential, Journal of Perianesthesia Nursing, vol. 18, No. 2, Apr. 2003, p. 96-117.

(56) References Cited

OTHER PUBLICATIONS

Gregoski, et al., Development and Validation of a Smartphone Heart Rate Acquisition Application for Health Promotion and Wellness Telehealth Applications, International Journal of Telemedicine and Applications, Jan. 2012, p. 1-8.
Jonathan, et al., Investigating a Smartphone Imaging Unit for Photoplethysmography, IPEM Physiological measurement, Sep. 2010, 6 pages.
Kaplan, , Can the Ubiquitous Power of Mobile Phones Be Used to Improve Health Outcomes in Developing Countries?, Globalization and Health, May 2006, 14 pages.
Karlen, et al., Design Challenges for Camera Oximetry on a Mobile Phone, Proceedings of the Annual International Conference of the IEEE Engineering in Medicine and Biology Society, EMBS, Aug. 2012, p. 2448-2451.
Karlen, et al., Detection of the Optimal Region of Interest for Camera Oximetry, Proceedings of the Annual International Conference of the IEEE Engineering in Medicine and Biology Society, Jul. 2013, p. 2263-2266.
Kim, et al., LED and CMOS Image Sensor Based Hemoglobin Concentration Measurement Technique, Elsevier, Apr. 8, 2011, p. 103-109.
Kraitl, et al., Optical Sensor Technology for a Noninvasive Continuous Monitoring of Blood Components, Proceedings of SPIE, Feb. 2010, p. 1-11.
Kwon, et al., Validation of Heart Rate Extraction Using Video Imaging on a Built-In Camera System of a Smartphone, Proceedings of the Annual International Conference of the IEEE Engineering in Medicine and Biology Society, EMBS, Aug. 2012, p. 2174-2177.
Larson, et al., Spirosmart: Using a Microphone to Measure Lung Function on a Mobile Phone, UbiComp '12, Sep. 2012, p. 280-289.
Macknet, et al., The Accuracy of Noninvasive and Continuous Total Hemoglobin Measurement by Pulse Co-Oximetry in Human Subjects Undergoing Hemodilution, Anesthesia and Analgesia, vol. 111, No. 6, Dec. 2010, p. 1424-1426.
Nandakumar, et al., Contactless Sleep Apnea Detection on Smartphones, The 13th Annual International Conference on Mobile Systems, Applications and Services, May 2015, p. 45-57.
Rice, et al., Noninvasive Hemoglobin Monitoring: How Accurate Is Enough?, Anesthesia and Analgesia, Oct. 2013, vol. 117, No. 4, p. 902-907.
Ruckman, A Comparative Study of Total Hemoglobin Measurement Technology: Noninvasive Pulse Co-Oximetry and Conventional Methods, University of Connecticut Graduate School, May 2011, p. 1-55.
Scully, et al., Physiological Parameter Monitoring From Optical Recordings With a Mobile Phone, IEEE Transactions on Biomedical Engineering, vol. 59, No. 2, Feb. 2012, p. 303-306.
Seah, et al., Eyenaemia, STAT Innovations, Jun. 2019, 2 pages.
Thompson, Smartphone Attachment for Stethoschope Recording, Methods in Molecular Biology, vol. 1256, Jan. 2015, p. 327-334.
Timm, et al., Novel Multi Wavelength Sensor Concept to Detect Total Hemoglobin Concentration, Methemoglobin Concentration, Methemoglobin and Oxygen Saturation, Progress in Biomedical Optics and Imaging—Proceedings of SPIE, vol. 9332, Mar. 2015, p. 1-10.
Von Schenck, et al., Evaluation of "HEMOCUE," A New Device for Determining Hemoglobin, Clinical Chemistry, vol. 32, No. 3, Mar. 1986, p. 526-529.
Wac, Smartphone as a Personal, Pervasive Health Informatics Services Platform: Literature Review, Imia Yearbook of Medical Informatics, Aug. 2012, p. 83-93.
Webster, Medical Instrumentation: Application and Design, John Wiley & Sons, Inc., Feb. 2009, 696 pages.
Woodward, et al., Design of a Telemedicine System Using a Mobile Telephone, IEEE Transactions on Information Technology in Biomedicine, Mar. 2001, p. 13-15.
Zhang, et al., Investigation of Noninvasive In Vivo Blood Hematocrit Measurement Using NIR Reflectance Spectroscopy and Partial Least-Squares Regression, Society of Applied Spectroscopy, vol. 54, No. 2, Feb. 2000, p. 294-299.
Zhu, et al., Opto-Fluidics Based Microscopy and Flow Cytometry on a Cell Phone for Blood Analysis, Methods in Molecular Biology, vol. 1256, Jan. 2015, p. 162-190.
Zouridakis, et al., Melanoma and Other Skin Lesion Detection Using Smart Handheld Devices, Methods in Molecular Biology, vol. 1256, Jan. 2015, p. 459-496.
Receipt of ISR/WO for P262715.WO.01 dated Mar. 10, 2017 for appln No. PCT/US2016/067988.

\* cited by examiner

DEVICES AND METHODS FOR PREDICTING HEMOGLOBIN LEVELS USING ELECTRONIC DEVICES SUCH AS MOBILE PHONES

CROSS-REFERENCE TO RELATED APPLICATION(S)

This application is a 35 U.S.C. § 371 National Stage Application of PCT Application No. PCT/US2016/067988, filed on Dec. 21, 2016, which claims the benefit under 35 U.S.C. § 119 of the earlier filing date of U.S. Provisional Application Ser. No. 62/271,222, filed Dec. 22, 2015, and U.S. Provisional Application Ser. No. 62/330,968, filed May 3, 2016, The entire contents of the aforementioned applications are hereby incorporated by reference, in their entirety, and for any purpose.

TECHNICAL FIELD

Embodiments of the invention relate generally to prediction of hemoglobin levels. Examples of methods and devices for predicting hemoglobin levels are described, including mobile phones and applications for predicting hemoglobin using mobile phones.

BACKGROUND

Hemoglobin generally refers to the protein molecule in the blood that carries oxygen throughout the body. A measure of hemoglobin may be considered a representation of the oxygen carrying capacity of a patient's blood. This may be distinct from oxygen saturation, which generally measures the oxygen carrying efficiency of the blood. A total hemoglobin (tHb) level refers to the concentration of hemoglobin g/dL in the blood. Low levels of hemoglobin are indicative of various health aspects such as low blood production, excessive bleeding, and/or malnutrition. Currently, the accepted clinical standard for measuring hemoglobin level is to perform laboratory tests requiring a blood draw. Point of care systems provide an option for performing the tests without a laboratory, one such being the Quest HemoCue. These tests however still require a prick of the finger to provide the blood needed for a chemical analysis.

Optical solutions using wavelengths of Red and IR light can be used to detect total hemoglobin levels. Existing optical solutions rely on a method called hemochromatic analysis, which is an analysis of the coloration of the blood.

SUMMARY

Examples of devices are described herein. An example device includes a plurality of light sources including at least one broadband light source configured to provide light in a range of wavelengths. The plurality of light sources may be positioned to illuminate a body part when placed in a target area. The device may include a camera including optical sensors. The camera may be positioned to receive reflected light from the body part when placed in the target area. The optical sensors may be configured to detect incident light having respective wavelengths within the range of wavelengths and provide image data for the respective wavelengths. The device may further include at least one processor and computer readable media encoded with instructions, including instructions which, when executed, cause the device to extract features from the image data for the respective wavelengths, the features selected based on the plurality of light sources and the optical sensors, and predict a hemoglobin level based on a comparison of the features to a model.

In some examples, the optical sensors are configured to detect incident light having wavelengths of less than 1000 nm.

In some examples, the broadband light source comprises a white light source and at least one optical sensor is configured to detect red wavelengths and at least another optical sensor is configured to detect blue wavelengths. In some examples, the plurality of light sources further include an infrared light source.

In some examples, the features may include an amplitude of pulsatile absorption of the image data from the optical sensor configured to detect red wavelengths responsive to illumination by the white light source, an amplitude of pulsatile absorption of image data from the optical sensor configured to detect blue wavelengths responsive to illumination by the white light source, an amplitude of pulsatile absorption of image data from the optical sensor configured to detect blue wavelengths responsive to illumination by the infrared light source, a pairwise ratio of pulsatile absorptions between the image data from the optical sensor configured to detect blue wavelengths responsive to illumination by the white light source and the image data from the optical sensor configured to detect red wavelengths responsive to illumination by the white light source, and an adjusted absorption difference between the image data from the optical sensor configured to detect red wavelengths responsive to illumination by the white light source and the image data from the optical sensor configured to detect blue wavelengths responsive to illumination by the infrared light source.

In some examples, the features include features associated with nonlinear interactions between wavelengths.

In some examples, the plurality of light sources include an incandescent light source.

In some examples, the device comprises a mobile phone.

In some examples, the computer readable media is further encoded with instructions which, when executed, cause the device to sequentially illuminate the target area with each of the plurality of light sources.

In some examples, the computer readable media is further encoded with instructions which, when executed, cause the device to provide an indication of a failed anemia screening when the hemoglobin level is below a threshold level.

In some examples, the features are selected using a regression for the plurality of light sources and the optical sensors based on blood test values.

In some examples, the regression is a linear regression or a support vector machine regression.

Examples of methods are described herein. An example method includes placing a body part in a target area proximate a mobile phone, illuminating the body part with a plurality of light sources on the mobile phone, detecting reflected light from the body part with a camera of the mobile phone including with each of a plurality of optical sensors configured to detect different wavelengths and provide image data for the different wavelengths, and predicting a hemoglobin level in the body part using an application on the mobile phone, wherein the application is configured to cause the mobile phone to extract features from the image data for the different wavelengths and compare the features to a model of hemoglobin levels.

In some examples, illuminating the body part comprises sequentially illuminating the body part with each of the plurality of light sources.

In some examples, methods further include illuminating the body part with another light source external to the mobile phone.

In some examples, predicting the hemoglobin level further comprises displaying an indication of the hemoglobin level on a screen of the mobile phone.

In some examples, methods further include displaying an indication of failure of an anemia screening when the hemoglobin level is below a threshold.

In some examples, methods further include installing the application on the mobile phone.

In some examples, illuminating the body part with the plurality of light sources comprises illuminating the body part with a flash of the mobile phone.

In some examples, methods further include developing the model of hemoglobin levels and selecting the features by performing a regression based on the plurality of light sources, optical sensors, and blood test data.

In some examples, extracting features comprises extracting features selected based on the plurality of light sources and optical sensors.

This summary includes examples of described subject matter. The summary should not be used to limit the scope of any claim.

DETAILED DESCRIPTION

Certain details are set forth below to provide a sufficient understanding of described examples. However, it will be clear to one skilled in the art that other examples may be practiced without certain of these particular details. In some instances, well-known circuits, control signals, timing protocols, electronic device components, software operations, and hemoglobin detection methodologies have not been shown in detail in order to avoid unnecessarily obscuring the described examples.

Examples described herein include electronic devices which may serve as hemochromatic analyzers, leveraging sensors and computation available on the electronic devices themselves, such as smartphones and smartwatches. In this manner, minor to no hardware modification may be required to a mobile phone or other electronic device to allow the device to predict hemoglobin levels. An application may be installed on an existing electronic device, such as a mobile phone, which may utilize the existing hardware of the electronic device (with modifications in some examples) to noninvasively predict hemoglobin level. This way, people may be able to perform hemoglobin measurements in non-clinical settings more easily and cheaply. Examples described herein may include one or more broadband light source(s) (such as from 600 nm to 1300 nm in some examples, from 600 nm to 1000 nm in some examples, 600 nm to 970 nm in some examples, 700 nm to 1000 nm in some examples, or other ranges in other examples), optical sensors (e.g. an array of photodetectors or a camera, or a camera with IR response), and computation on the electronic device or on a remote computing system.

Examples described herein may analyze the color of blood (e.g. through transmitted and reflected light) to predict a hemoglobin level. Prior solutions had not demonstrated capability using reflected light. Noninvasive measurement may be desirable for both sanitation and ease of use when measuring frequently because it avoids or reduces puncturing the skin.

Figure 1:
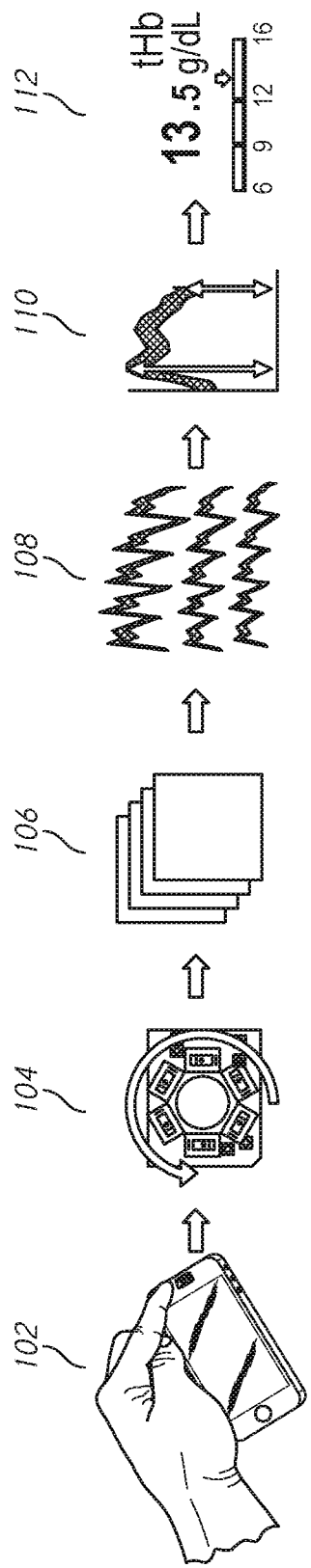
FIG. 1 is a schematic illustration of a method arranged in accordance with examples described herein.

FIG. 1 is a schematic illustration of a method arranged in accordance with examples described herein. FIG. 1 provides a small schematic illustration associated with each phase of an example method—phase 102, phase 104, phase 106, phase 108, phase 110, and phase 112. In other examples, other, different, and/or fewer phases may be used.

In phase 102, a body part may be placed in a target area proximate an electronic device. A mobile phone is shown implementing the electronic device in FIG. 1, however, other electronic devices may be used. Electronic devices which may be used include, but are not limited to, wearable devices such as watches or wristbands, medical devices, computers such as laptops, desktops, servers, or tablets, automobiles, appliances, or combinations thereof. As described herein, the electronic device used in phase 102 may have light source(s) and a camera that may be used in predicting hemoglobin levels. In some examples, an application for predicting hemoglobin levels may be installed on the electronic device. The installation may in some examples occur prior to phase 102.

Body parts which may be used for predicting hemoglobin levels described herein include, but are not limited to, one or more fingers (as shown in FIG. 1), one or more toes, ears, or combinations thereof.

In phase 102, the body part is placed in a target area proximate the electronic device. The target area generally refers to an area that is able to receive light from the light source(s) of the electronic device, and an area from which the camera of the electronic device may receive reflected light. Generally, the body part is placed such that it may receive light emitted from the light source(s) included in the electronic device. The body part is also placed such that the camera included in the electronic device may receive light reflected from the body part. Accordingly, in some examples, a finger may be placed covering and/or partially covering the light source(s) and camera. In some examples, a toe may be placed covering and/or partially covering the light source(s) and camera. In some examples, the electronic device may be placed against an ear such that a portion of the ear covers and/or partially covers the light source(s) and camera. In some examples, the body part may contact the light source(s) and/or camera. In some examples, the body part may be separated from the light source(s) and/or camera.

In phase 104, the body part may be illuminated with the light source(s) on the electronic device (such as the mobile phone shown in FIG. 1). In some examples, phase 104 may additionally include illuminating the body part with an external light source. In some examples, the light source(s) are used to sequentially illuminate the body part. For example, one light source may illuminate the body part for a period of time. Then, another light source may illuminate the body part for another period of time. The periods of time for each light source may be the same or may be different. In some examples, the period may be 10 seconds for each light source, 15 seconds for each light source in other examples, 20 seconds for each light source in other examples. Other periods may be used in other examples. Generally, the period of illumination by each light source may be sufficient to capture several heartbeats. Given an average heartrate of 75 beats per minute, for example, 15-20 heartbeats may be captured with a 15 second illumination time period.

In some examples, at least one broadband light source may be used. A broadband light source may emit wavelengths of light over several wavelength ranges. For example, a broadband light source may emit wavelengths of light that may be detected by more than one optical sensors in a camera of the electronic device or otherwise included in the electronic device, such as infrared optical sensors in a proximity sensor unit and/or an infrared laser autofocus system. In some examples, a flash and/or light emitting source of a prosimity sensor and/or infrared laser autofocus system included in the electronic device may be used as at least one of the light source(s).

In other examples in phase 104, some or all of the light source(s) may illuminate the body part simultaneously, or at least partially simultaneously. Generally, sequential illumination may be preferred in some examples where a limited sampling rate of a commodity camera is used and it may not be desirable to synchronize the light source(s) with the camera's frame refresh, making it not feasible to measure all wavelengths of light at the same time. However, in some examples, access to low level hardware control or other custom components may be provided to support simultaneous measurement of all or multiple light sources.

In phase 106, reflected light from the body part may be detected with a camera of the electronic device. For example, video and/or image data may be obtained by the camera of the electronic device. Video data may serve as a source of image data described herein. Example video data may be obtained at 10, 15, 20, 25, or 30 frames per second in some examples. Other frame rates may also be used including 100, 200, 300, 400, 500, 600, 700, 800, 900, or 1000 frames per second. Each frame may be referred to as image data. Video and/or image data may be obtained for each of the light source(s) used. For example, one set of video and/or image data may be obtained corresponding to reflected light received from the body part responsive to illumination by a first light source. Another set of video and/or image data may be obtained corresponding to reflected light received from the body part responsive to illumination by a second light source. The number of sets of data may correspond to the number of light sources in some examples. In some examples, video and/or image data may be obtained corresponding to reflected light received from the body part responsive to illumination by multiple light sources.

Note that cameras may generally include a number of optical sensors, each sensitive to different wavelengths (e.g. different wavelength ranges). For example, cameras may include a red, green, and blue optical sensor. Accordingly, the camera used in FIG. 1 may capture image and/or video data which includes channels of data corresponding to each of the different optical sensors (e.g. a red channel, a green channel, and a blue channel). In other examples, cameras may have different optical sensors sensitive to different wavelengths. Generally, image and/or video data obtained by the camera may include channels, where each channel represents data corresponding to particular wavelengths (e.g. collected by an optical sensor sensitive to particular wavelengths). Accordingly, the camera of the electronic device may provide image data for different wavelengths. Moreover, infrared sensors may be used additionally or instead of the camera. Generally, a user's body part may be placed in such a way as to cover or otherwise reflect light to those sensors when used.

In some examples, camera settings on existing electronic devices (e.g. mobile phones) may be manipulated to facilitate obtaining useful video and/or image data for techniques described herein. For example, camera settings pertaining to white balancing (e.g. "incandescent mode") may be selected which avoid or reduce rebalancing of detected image data to remove or reduce infrared (IR) components. Instead, detected IR components may be retained in the video and/or image data. In some examples, hardware gains may be set for each channel (e.g. RGB channel) using presets for each light source. For example, the presets may be determined empirically found for each lighting source such that the three channels report a similar level of light. This may aid in retaining all or more of the data from all channels. For example, the red channel may have a much stronger response due to the red blood under white and incandescent lights. If left to a flat white balance, the auto exposure on a camera may be set to the red channel, leaving the other channels underexposed. Exposure may be set using the camera autoexposure settings.

In phase 108, time series data for each channel may be obtained for each light source. The time series data may be intensity data. The time series data may be obtained, for example, by averaging or otherwise combining data for the channel from each frame of video data, or from a sequence of image data. In some examples, an entire frame or image may be used to generate a time series data point—e.g. an average of all pixels in the frame may be used. In other examples, portions of the frame and/or image may be used. In some examples, only pixels from a central portion of the frame and/or image may be used. In some examples, pixels having values outside a threshold may be discarded.

Accordingly, phase 108 may result in a time series data representing intensities for each channel during illumination by each light source. For example, illumination by a first light source may result in three sets of time series data—one representing intensity over time for the red channel, one representing intensity over time for the green channel, and one representing intensity over time for the green channel. Illumination by a second light source may yield another three sets of time series data—one representing intensity over time for the blue channel, one representing intensity over time for the green channel, and one representing intensity over time for the green channel. Different numbers of channels and light sources may be used. In some examples, a time series of data may not be obtained for each channel. For example, the green channel may not be needed in some examples. Accordingly, in some examples, time series data may be obtained for only the red and blue channels.

In phase 110, features are extracted from the time series data. Any of a variety of features may be used. Examples of features are described herein and may include peaks, troughs, and interaction terms between light sources. In some examples, an application running on the electronic device used to illuminate the body part may be used to extract the features.

In phase 112, the features extracted in phase 110 may be compared to a model of hemoglobin levels to provide a predicted hemoglobin level of blood in the body part. In some examples, the comparison may include application of a regression to predict a hemoglobin level of blood in the body part based on the features extracted in phase 110. Generally, the regression may involve a comparison between the extracted features and a model of hemoglobin levels. The model of hemoglobin levels may be based, for example, on training data and blood tests. For example, the model of hemoglobin levels may be developed based on the plurality of light sources, optical sensors, and blood test data. The plurality of light sources and optical sensors of the electronic device to be used may be used to collect data from test subjects. Blood tests of the test subjects may also be performed to determine hemoglobin levels. The model relating extracted features to predicted hemoglobin level may be developed based on that training and test data.

In some examples, an application running on the electronic device used to illuminate the body part may be used to conduct the comparison and/or apply the regression. The comparison and/or application of the regression may result in a predicted hemoglobin level. An indication of the predicted hemoglobin level may be displayed, for example on a display of the electronic device used to illuminate the body part. For example, a number representing the predicted hemoglobin level may be displayed. In some examples, an indication of whether the predicted hemoglobin level was above, below, and/or near a threshold may be displayed (e.g. a green, red, and/or yellow indicator). For example, an indication of a failure of a screening may be displayed if the predicted hemoglobin level is below a threshold. The screening may be a screening for any of a variety of hemoglobin-related conditions (e.g. anemia, malnutrition, need for transfusion). In some examples, a range of predicted hemoglobin levels below 9 g/dL (e.g. between 6 g/dL and 9 g/dL) may be considered below a threshold, and may result in a red indicator. In some examples, a range of predicted hemoglobin levels between 9 g/dL and 12 g/dL may be considered near a threshold, and may result in a yellow indicator. In some examples, a range of predicted hemoglobin levels above 12 g/dL (e.g. between 12 g/dL and 16 g/dL) may be considered above a threshold, and may result in a green indicator.

The features extracted in phase 110 and/or the features used in phase 112 may be based on the light source(s) and cameras used. As described herein, certain features may lend themselves to the ability to predict hemoglobin with an acceptable level of accuracy for a particular combination of light source(s) and cameras with certain optical detectors.

Figure 2:
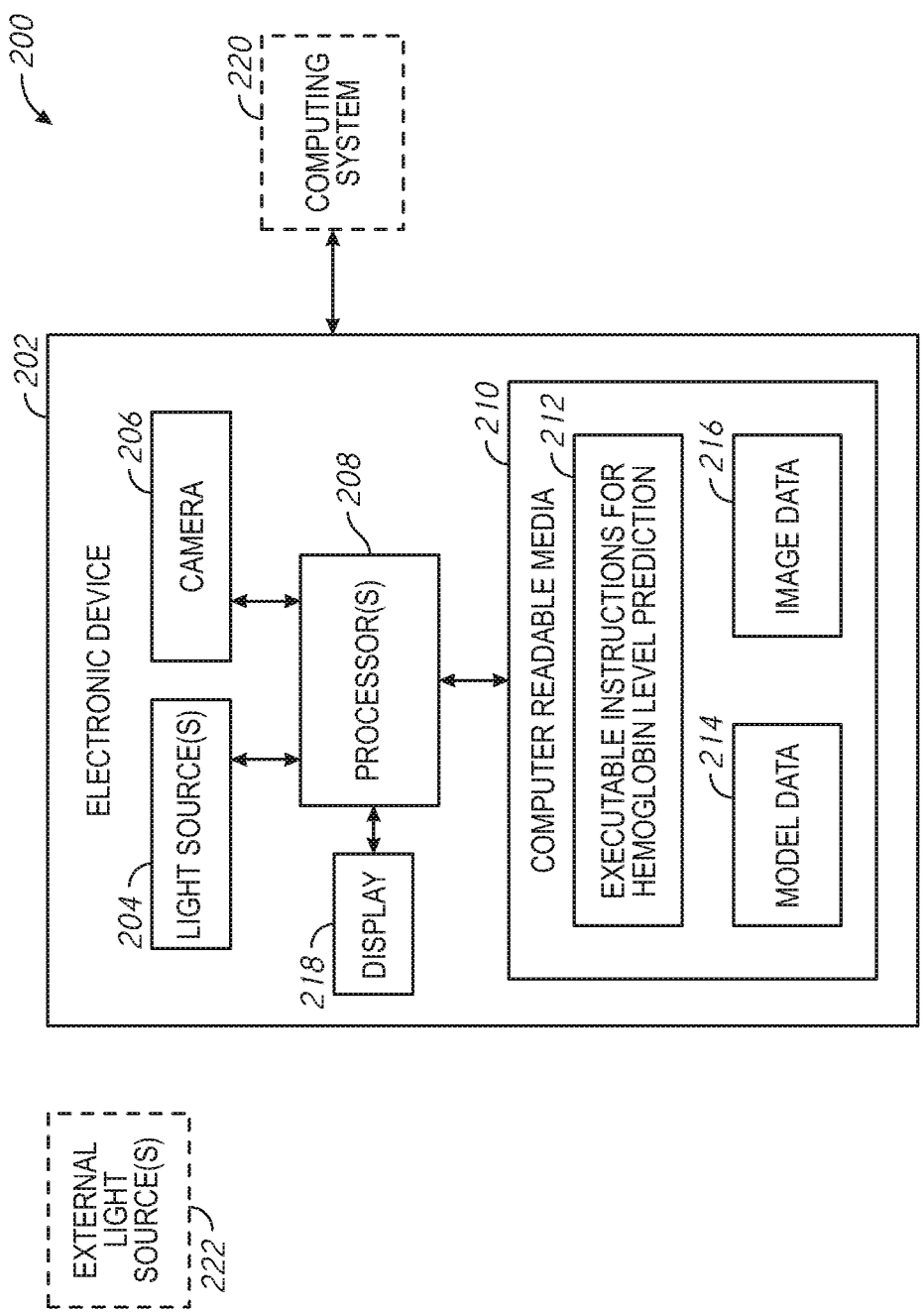
FIG. 2 is a schematic illustration of a system arranged in accordance with examples described herein.

FIG. 2 is a schematic illustration of a system arranged in accordance with examples described herein. The system 200 includes electronic device 202, optional computing system 220, and optional external light source(s) 222. Electronic device 202 includes light source(s) 204, camera 206, processor(s) 208, computer readable media 210, executable instructions for hemoglobin level prediction 212, model data 214, image data 216, and display 218. In other examples, fewer, other, different, and/or rearranged components may be present in the electronic device 202 and/or system 200.

The light source(s) 204 and the camera 206 may be in communication with the processor(s) 208. The display 218 may also be in communication with the processor(s) 208. The processor(s) 208 is also in communication with computer readable media 210 which may include executable instructions for hemoglobin level prediction 212. The executable instructions for hemoglobin level prediction 212, when executed by the processor(s) 208, may cause the electronic device 202 to perform actions described herein for predicting hemoglobin levels. The computer readable media 210 may further include model data 214 and/or image data 216.

The electronic device 202 may be in communication with computing system 220 using wired and/or wireless communication. It is to be understood that the arrangement of components in the electronic device 202 and/or computing system 220 may be quite flexible. For example, while the processor(s) 208 and executable instructions for hemoglobin level prediction 212 are described herein with reference to FIG. 2 as included in the electronic device 202, in some examples, the computing system 220 may instead perform some or all of the actions for predicting hemoglobin level. For example, data from the camera 206 may be provided to the computing system 220 for processing to predict a hemoglobin level in accordance with methods described herein in some examples.

The system of FIG. 2 may be used to perform the method of FIG. 1 in some examples.

Examples of devices that may be used to implement electronic device 202 include, but are not limited to mobile phones (e.g. smartphones), wearable devices such as watches or wristbands, medical devices, computers such as laptops, desktops, servers, or tablets, automobiles, appliances, or combinations thereof.

The electronic device 202 includes light source(s) 204. Generally any number of light source(s) 204 may be included. Examples include 1, 2, 3, 4, 5, 6, 7, 8, 9, and 10 light source(s). The light source(s) 204 may be implemented using LEDs in some examples. The light source(s) 204 may include at least one broadband light source. The broadband light source may provide light in a range of wavelengths and may be implemented, for example, using a white light (e.g. a white LED). In some examples, the light source(s) 204 may include a flash of the electronic device 202. The light source(s) 204 may be positioned to illuminate a body part when the body part is placed in a target area. In some examples, the light source(s) 204 may include an infrared light source, for example a 970 nm light source, such as a 970 nm LED (970 nm+/−10 nm in some examples) and/or a 880 nm light source, such as a 880 nm LED (880 nm+/−10 nm in some examples).

The light source(s) 204 may be integrated into the electronic device 202. For example, the light source(s) 204 may be integrated into the electronic device 202 as a flash, or may be packaged with the electronic device 202, for example, around an aperture used for the camera 206. In some examples the light source(s) 204 may be integrated into a case or other component that may be attached to the electronic device 202. For example, one or more of the light source(s) 204 may be mounted on a substrate that is attached, clipped, adhered, or otherwise mounted to the electronic device 202.

In some examples, external light source(s) 222 may be used in addition to the light source(s) 204. For example, the external light source(s) 222 may be implemented using an incandescent light source, tungstun light, or combinations thereof.

The camera 206 is generally positioned to receive reflected light from the body part when placed in the target area. The camera 206 may include a number of optical sensors. The optical sensors may generally detect incident light having respective wavelengths. In some examples, the respective wavelengths are within the range of wavelengths provided by the broadband light source. The optical sensors may provide image data (e.g. video data, where each frame of video data may be considered image data) for the respective wavelengths. For example, the camera 206 may include three optical sensors—one for red wavelengths, another for green wavelengths, and another for blue wavelengths. In some examples, the optical sensors may detect incident light having wavelengths of less than 1000 nm. Accordingly, in some examples, hemoglobin levels may be predicted without any detector capable of detecting wavelengths of light over 1000 nm. Alternately stated, the optical sensors may only detect incident light having wavelengths of less than 1000 nm.

Generally, the camera 206 and light source(s) 204 may be disposed on a same side of the electronic device 202 such that a body part may be placed to receive light transmitted from the light source(s) 204 and reflect the light to the camera 206. For example, the camera 206 and light source(s) 204 may be positioned on a back or front face of a mobile phone used to implement the electronic device 202. In another example, the camera 206 and light source(s) 204 may be positioned on a same edge of a watch used to implement electronic device 202.

In some examples, a so-called front-facing camera may be used to implement the camera 206. The front-facing camera may be desirable in some examples because the infrared (IR) cutoff of the front-facing camera in a typical mobile phone may be weaker than that of the rear-facing camera. The front-facing camera generally refers to a camera facing the user when the mobile phone is in use, such as a camera on a same side of the mobile phone as a display (e.g. Display 218), In other examples, the rear-facing camera may be used to implement camera 206. In some examples, through hardware or software modification, an IR cutoff of the camera may be improved.

The processor(s) 208 may be implemented using one or more processors. In some examples, multi-core processors may be used. In some examples processor(s) 208 may be implemented using, or partially or fully replaced by, custom circuitry (e.g. ASICs) or other processing elements.

The computer readable media 210 may be implemented generally by any electronic storage (e.g. volatile, non-volatile, removable and non-removable, RAM, ROM, EEPROM, flash or other memory technology, CD-ROM, digital versatile disk (DVD) or other optical storage, magnetic cassettes, magnetic tape, magnetic disk storage or other magnetic storage devices, solid state drives (SSD) or other solid state storage devices, or any other medium which can be used to store the desired information and which can be accessed by the electronic device 202). The computer readable media 210 may generally be implemented using any number of storage devices, and the listed data stored on the computer readable media 210—e.g. executable instructions for hemoglobin level prediction 212, model data 214, and image data 216, may each be stored on a same and/or different electronic storage medium. In some examples the computer readable media 210 may be implemented using multiple storage devices and any or all of the data shown stored on computer readable media 210 may be distributed across several storage devices.

The executable instructions for hemoglobin level prediction 212 may be executed by the processor(s) 208 to perform actions, such as those described with reference to FIG. 1. For example the executable instructions for hemoglobin level prediction 212 may include instructions for extracting features from image data for respective wavelengths.

For example, as discussed with reference to FIG. 1, the instructions may cause the electronic device 202 to illuminate a target area with the light source(s) 204. For example, the instructions may cause the electronic device 202 to sequentially illuminate the target area with the light source(s) 204. In some examples, the instructions may include instructions for prompting a user to turn on external light source(s) 222 or confirm that external light source(s) 222 are illuminated.

The executable instructions for hemoglobin level prediction 212 may generally be referred to as an application for predicting hemoglobin levels and may be installed on the electronic device 202. In some examples, the electronic device 202 may have communication and other components to receive and install software updates, such as updates improving one or more image capture, processing, and analysis algorithms, and/or the executable instructions for hemoglobin level prediction 212, which may allow the electronic device 202 and the executable instructions for hemoglobin level prediction 212 to be easily and quickly upgraded as necessary.

The executable instructions for hemoglobin level prediction 212 may include instructions for obtaining video data and/or image data from the camera 206 as described herein, for example with reference to FIG. 1. The executable instructions for hemoglobin level prediction 212 may include instructions for obtaining time series data for each optical sensor of the camera and for each light source, as described herein such as with regard to FIG. 1. The executable instructions for hemoglobin level prediction 212 may further include instructions for extracting features from the time series data as described herein, such as with regard to FIG. 1. In this manner, the executable instructions for hemoglobin level prediction 212 may include instructions for extracting features from image data obtained by the camera 206. As described herein, the features may be selected based on the light source(s) 204 and the camera 206 (e.g. the optical sensors in the camera 206). For example, features are selected using a regression for the plurality of light sources and the optical sensors based on blood test values. The regression may be a linear regression or a support vector machine regression.

The executable instructions for hemoglobin level prediction 212 may include instructions causing the electronic device 202 to predict a hemoglobin level based on a comparison of the features to a model, as described herein such as with regard to FIG. 1. The comparison may include applying a regression to the extracted features as described herein such as with regard to FIG. 1.

The executable instructions for hemoglobin level prediction 212 may further include instructions for providing an indication of a failed screening as described herein, such as with regard to FIG. 1.

The indication may be provided on display 218. The display 218 may be implemented using, for example, a monitor, screen, touchscreen, or combinations thereof. In some examples, the display 218 and an input unit can be implemented across shared hardware (e.g., the same touchscreen is used to accept input and display output). The display 218 may also be used to display one or more suitable user interfaces (UIs) to the user, such as UIs of an application for predicting hemoglobin levels.

Although not shown explicitly in FIG. 2, the electronic device 202 may also include an input unit for receiving input from a user. Examples of input units include, but are not limited to, keyboards, mice, touchscreens, joysticks, and combinations thereof. The input unit may in some examples accept voice commands and/or gestural commands.

Although not shown explicitly in FIG. 2, the electronic device 202 may also include a communication unit to receive and/or transmit data (e.g., image data, video data, a pulse waveform, predicted hemoglobin levels, model data, software updates, etc.) between the electronic device 202 and computing system 220 or a different separate device or system, such as another remote server or other computing system. The communication unit may use any suitable combination of wired or wireless communication methods, including Wi-Fi communication. In some examples, the communication between the electronic device 202 and the separate system may be performed using short message service (SMS) text messaging. The communication unit may also be operably coupled to the processor(s) 208, such that data communication to and from the electronic device 202 may be controlled based on instructions provided by the executable instructions for hemoglobin level prediction 212.

The optional computing system 220 may be implemented across any suitable combination of physical and/or virtualized computing resources (e.g., virtual machines), including distributed computing resources (e.g. "in the cloud"). In some examples, the computing system 220 may be a remote server in communication with a plurality of electronic devices including the electronic device 202. The communication can utilize any suitable wired or wireless communication methods, as described above.

The computing system 220 may include one or more processors, a memory or other data storage device storing executable instructions, and a communication unit. The communication unit can be used to communicate data (e.g., image data, hemoglobin estimates, software updates, model data, etc.) between the computing system 220 and the electronic device 202 (e.g., via SMS text messaging). For example, the computing system 220 may receive image data provided by the electronic device 202, such as image data that has not yet been processed in some examples. The data obtained from the electronic device 202 may be stored in the computing system 220 in some examples. The computing system 220 may provide instructions executable by the processors to process and analyze the image data, such as by performing one or more acts of the methods described herein. The computing system 220 may output a prediction of the patient's hemoglobin level, which can be stored in the memory and/or transmitted to the electronic device 202. In some instances, depending on user preference, the results can additionally or instead be transmitted to a third party, such as a medical professional who can review the results and provide the user with further instructions as necessary.

In this manner, electronic devices may be provided which have all the necessary hardware to perform a medical analysis (e.g. predict a hemoglobin level), but use the electronic device (e.g. Mobile phone) as a hub to control the device, receive data, store data, and potentially send data to an outside database for access by hospitals and doctors.

Accessory components may be provided in some examples. For example, a cuff (e.g. a finger cuff) may be provided and mounted to the electronic device 202 such that it aids in positioning a body part proximate the camera 206 and/or light source(s) 204. Such a cuff may also function as a cover to block or reduce ambient light. A small window may be integrated into the top of the cuff to be opened for the incandescent light.

Figure 3:
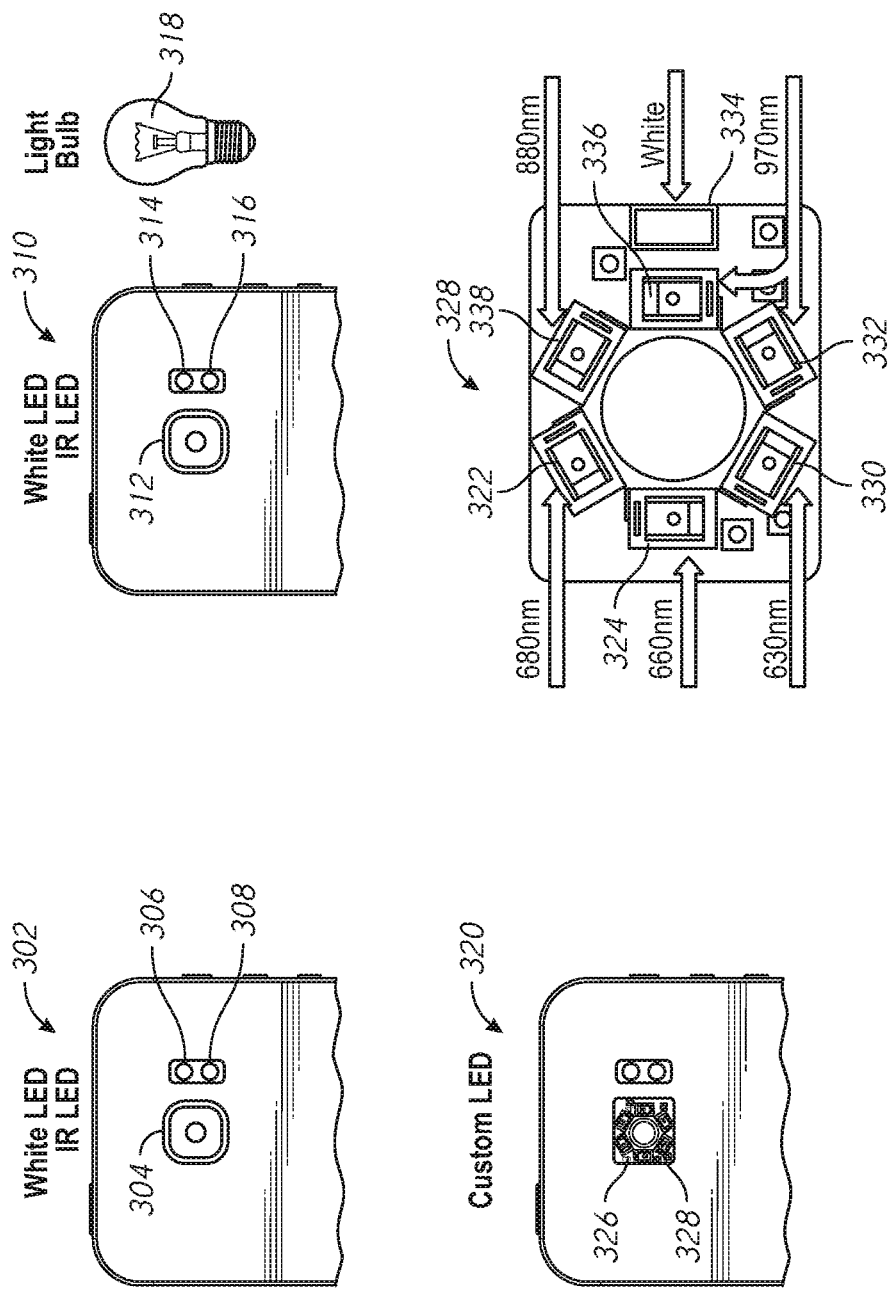
FIG. 3 is a schematic illustration of different hardware implementations of cameras and light sensors arranged in accordance of examples described herein.

FIG. 3 is a schematic illustration of different hardware implementations of cameras and light sensors arranged in accordance of examples described herein. Three different implementations are shown—arrangement 302, arrangement 310, and arrangement 320. Each arrangement depicts light sources and a camera and their position integrated into a mobile phone. The arrangement 302 includes camera 304, light source 306, and light source 308. The arrangement 310 includes camera 312, light source 314, light source 316, and external light source 318. The arrangement 320 includes camera 326 and plurality of light sources 328. The plurality of light sources 328 may include light source 322, light source 324, light source 330, light source 332, light source 334, light source 336, and light source 338.

Operation of systems having each of the arrangements shown in FIG. 3 to predict hemoglobin levels is further described herein. It should be appreciated that other arrangements are possible in other examples, and the detailed description of the arrangements shown in FIG. 3 is to facilitate understanding and not by way of limitation.

In the arrangement 302, the light source 306 is implemented using a white flash of the mobile device. In the arrangement 302, the light source 308 is implemented using an infrared (IR) emitter. Existing mobile devices (e.g. mobile phones) may be already provided with a white LED for a flash. Accordingly, the light source 306 may not require augmentation of an existing device in some examples. Existing mobile devices (e.g. mobile phones) may have an IR emitters (e.g. which may be used for autofocus). Accordingly, no hardware augmentation of an existing electronic device (e.g. a smartphone) may be required for arrangement 302.

In the arrangement 310, the light source 314 is implemented using a white or other flash of the mobile device. Generally, any light source positioned in an electronic device such that the light may be reflected off a body part to an optical sensor may be used. In the arrangement 310, the light source 316 is implemented using an infrared emitter. The arrangement 310 also includes external light source 318, which is implemented using an incandescent lamp. As described, the white flash and infrared emitter may be present on existing mobile phones or other electronic devices, and therefore no augmentation may be necessary to provide those components in some examples. The addition of external light source 318 may be a minor augmentation.

In some examples, an incandescent light bulb, such as the external light source(s) 222, may provide a source of IR light. For example, incandescent light bulbs typically have strong IR light emission in the NIR range. In some examples, a 6 W incandescent light bulb was used, which may be commonly available.

In arrangement 310, the light source 314 and the light source 316 are placed in or around the phone camera, while the external light source(s) 222 may be placed above the camera 312 during use, about 1 inch above the finger in some examples, about 2 inches above the finger in some examples, about 3 inches above the finger in some examples, about 4 inches above the finger in some examples, about 5 inches above the finger in some examples. Other distances may be used in other examples.

In the arrangement 302 and the arrangement 310, the light sources are positioned on a same side of the electronic device as the camera. The light sources are positioned a distance from the camera, but sufficiently close that a part of a body (e.g. a finger) may be placed in contact with both the camera and the light sources.

In the arrangement 320, a plurality of light sources 328 are disposed around the camera 326. The plurality of light sources 328 may be implemented using a custom LED array, which is shown in further detail in FIG. 3. The plurality of light sources 328 may be provided by way of hardware augmentation of an existing electronic device in some examples (e.g. a mobile phone). The augmentation may include building the plurality of light sources 328 into the device in some examples, or providing a substrate having the plurality of light sources 328 that may be mounted to an existing electronic device. For example, the plurality of light sources 328 may be provided in a phone case in some examples that may fit over an existing mobile phone and, when fitted to the mobile phone, position the plurality of light sources 328 around the camera 326.

The plurality of light sources 328 may include a 680 nm LED 322, a 660 nm LED 324, a 630 nm LED 330, two 970 nm LEDs 332 and 336, a white LED 334, and an 880 nm LED 338. Fewer, greater, or subsets of those LEDs may be used in other examples. In some examples, a white LED, two 970 nm LEDs and an 880 nm LED may be used. In some examples, a white LED, a 970 nm LED, and an 880 nm LED may be used.

Examples of algorithms and methodologies for predicting hemoglobin using systems and methods described herein may involve comparing relative absorptivity of blood at multiple wavelengths. Examining absorptivity at multiple wavelengths may allow for a comparison of the ratios of multiple forms of hemoglobin (e.g. Oxyhemoglobin, Deoxygenated Hemoglobin, Methemoglobin, carboxyhemoglobin) and also blood plasma which may be considered mainly a water solution The various forms of hemoglobin have different absorptivity, generally between 600 nm to 1000 nm. Water generally begins to have absorption above 900 nm. At each heartbeat, some amount of blood is pushed through and temporarily increases the amount of blood in a cross section of the vessel as the pulse propagates. The baseline strength of a reflected signal may be referred to as DC absorption. The fluctuation due to the pulse may be referred to as AC absorption. By measuring the DC and AC absorption at multiple wavelengths along the spectrum, systems described herein may predict a ratio of each hemoglobin against the amount of water, which produces a total predicted ratio of hemoglobin to water.

Examples described herein may overcome a typical limitation of using existing mobile phone or other commodity hardware for hemoglobin measurement: a lack of sensitivity to incident light greater than 1000 nm. Generally, examples described herein may rely on IR absorption only under 1000 nm. Water generally begins to have a response above 940 nm and has an initial relative maximum at 970 nm.

Examples described herein may not only evaluate the water content in the plasma, but also the proteins that make up about 10% of the blood plasma by volume as a proxy for capturing the plasma volume to compare against hemoglobin concentration. This may be accomplished by leveraging the blue absorption of the plasma. By illuminating the finger with a white LED (which contains a strong blue component) and an IR light (e.g. at 970 nm), examples of systems described herein are capable of capturing the plasma response.

In some examples, an additional IR light source (e.g. 880 nm) may be used to help capture the different absorption between the various forms of hemoglobin. Both the 970 nm and 880 nm LEDs are generally in the range used for IR autofocus LEDs that may be provided in commodity mobile phones.

Algorithms that may be used by devices and methods herein to predict hemoglobin levels may proceed in generally to parts. First, the pulsatile signal recorded in captured video and/or image data may be extracted (e.g. the pulsatile signal may be identified from time series data generated for each wavelength range and each light source). Next, features may be extracted that may include combining intensity values extracted from multiple light source's video data and/or image data. The extracted features may then be used with an SVM to train regression models based on blood tests that serve as a ground truth.

Generally, hemachrome analysis is the study of blood coloration to analyze the components in the blood. Example algorithms and methodologies used herein may aim to measure the concentration of hemoglobin as compared to the concentration of plasma in the blood.

The Beer-Lambert law states that the absorption of light is proportional to the concentration and thickness of the medium, given by:

$$I_{measured} = I_0 e^{-\alpha[C]d} \qquad \text{Equation 1}$$

where $I_0$ is the incident light intensity, a is the absorption coefficient, [C] is the concentration, and d is the thickness of the medium that the light travels through. When a body part is illuminated with a single wavelength of light, the measured intensity, $I_{measured}$ may represent absorption due to tissues, hemoglobin, and plasma:

$$I_{m,\lambda} = I_{0,\lambda} e^{-d(\alpha_{tissue,\lambda}[tissue] + \alpha_{Hb,\lambda}[Hb] + \alpha_{plasma,\lambda}[Plasma])} \qquad \text{Equation 2}$$

where $\lambda$ is the wavelength of the incident light. To obtain the ratio of [Hb] and [plasma], the attenuation of the intensity signal due to tissue should be eliminated or reduced. Generally, this may be accomplished by measuring the temporal change of the measured intensity as the thickness of the arteries oscillate with respect to the heartbeat.

Figure 4:
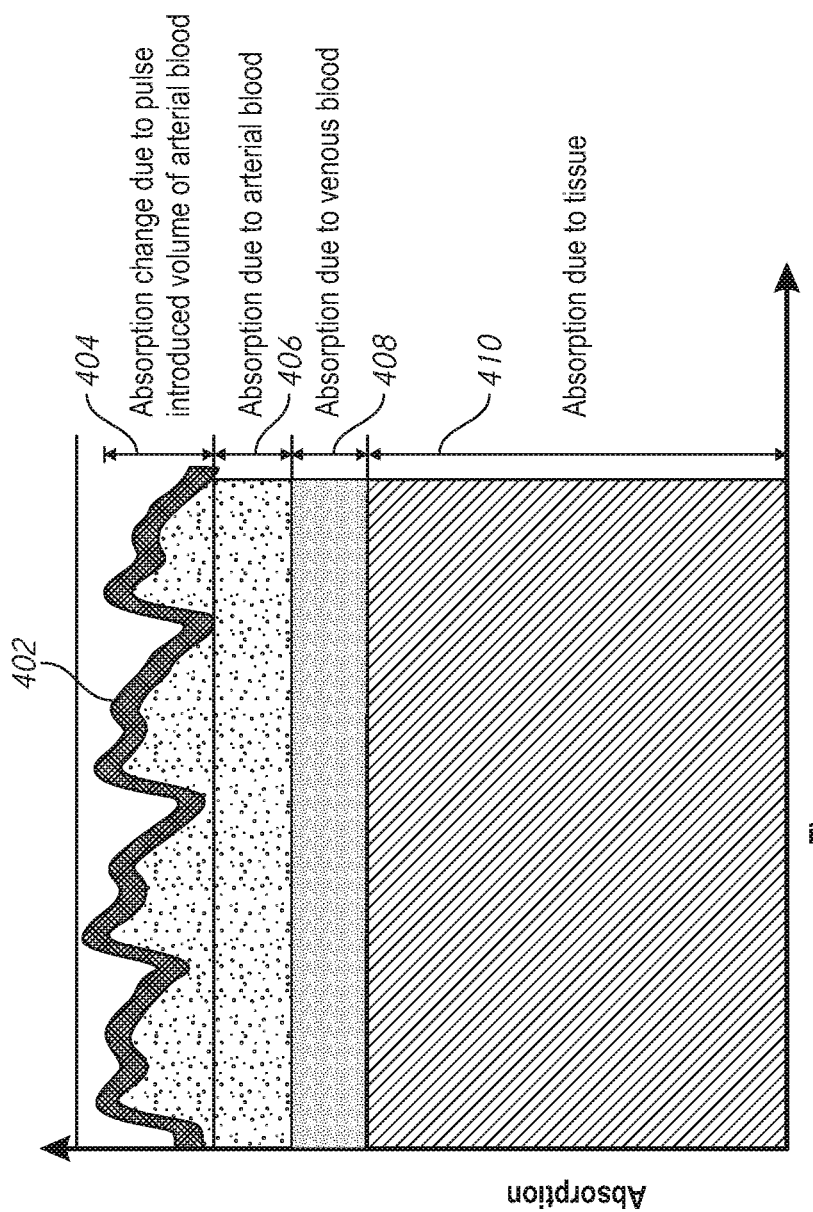
FIG. 4 is a schematic representation of absorption over time in accordance with examples described herein.

FIG. 4 is a schematic representation of absorption over time in accordance with examples described herein. FIG. 4 illustrates an intensity signal 402 which may, for example, be received by cameras and/or optical detectors described herein responsive to illumination with one or more light source(s) described herein. The intensity signal 402 can be viewed as having a number of components contributing to the overall intensity. Component 410 represents absorption due to tissue (e.g. the tissue of the body part that the incident light travels through and/or reflects from). The component 408 represents absorption due to venous blood in the body part. The component 406 represents absorption due to arterial blood in the body part. The component 404 represents a change in absorption that may be due to the pulse in a volume of arterial blood. It is this temporal change which may be further used by algorithms described herein, as it may eliminate or reduce the effect of absorption due to tissue.

The change in arterial thickness $\Delta d$ occurring during a heartbeat generally affects only the path length for Hb and plasma. By measuring the ratio of the maximum and minimum intensity of the light received, the effect of the tissue may be reduced and/or removed:

$$\frac{I_{peak,\lambda}}{I_{trough,\lambda}} = e^{\Delta d(\alpha_{Hb,\lambda}[Hb] + \alpha_{plasma,\lambda}[Plasma])} \qquad \text{Equation 3}$$

The ratio between the intensity at a peak of the intensity signal 402 an a trough of the intensity signal 402 at a given wavelength (or wavelength range) may be seen in Equation 3 to vary in accordance with the hemoglobin concentration [Hb] and the plasma concentration [Plasma] and the associated absorption coefficients of both.

The ratio of intensities can then be expressed as:

$$I_{R,\lambda} = \ln\left(\frac{I_{peak,\lambda}}{I_{trough,\lambda}}\right) = \alpha_{Hb,\lambda}[Hb]\Delta d + \alpha_{plasma,\lambda}[Plasma]\Delta d \qquad \text{Equation 4}$$

where the feature $I_{R,\lambda}$ is expressed as the natural log (ln) of the ratio of the peak and trough intensities (e.g. of the intensity signal 402). The feature $I_{R,\lambda}$ at a particular wavelength may be equal to the absorption coefficient of hemoglobin at the wavelength multiplied by the hemoglobin concentration [Hb] and the difference in arterial thickness Δd occurring during a heartbeat added to the product of the absorption coefficient of plasma at the wavelength multiplied by the plasma concentration [Plasma] and the difference in arterial thickness Δd occurring during a heartbeat.

In this manner, a measured ratio of maximum and minimum values of intensity may provide a measure of absorption due to the different components of blood. In some examples, systems may use empirically measured absorption coefficients for each compound at a specific wavelength of light to predict the hemoglobin concentration using Equation 4. By measuring the response at multiple wavelengths of light, multiple $I_{R,\lambda}$ features can be calculated. Ratios of $I_{R,\lambda}$ across wavelengths may determine the ambiguity of Δd allowing an estimate of [Hb] to be made. However, factors such as the distribution of the emitter, sensitivity of the sensor, and complex reflection properties of tissue may make this approach undesirable.

In some examples, light source(s) used to provide illumination include broadband light source(s) such as incandescent and/or white LEDs. The broadband light sources may be poorly modeled by Equation 4. Accordingly, in some examples, machine learned regressions may be used to estimate the absorption coefficients (e.g. $\alpha_{Hb,\lambda}$ and $\alpha_{plasma,\lambda}$) for each lighting source. This may allow algorithms for predicting hemoglobin to eliminate and/or reduce reliance on predetermined absorption coefficients at specific wavelengths for blood.

Figure 5:
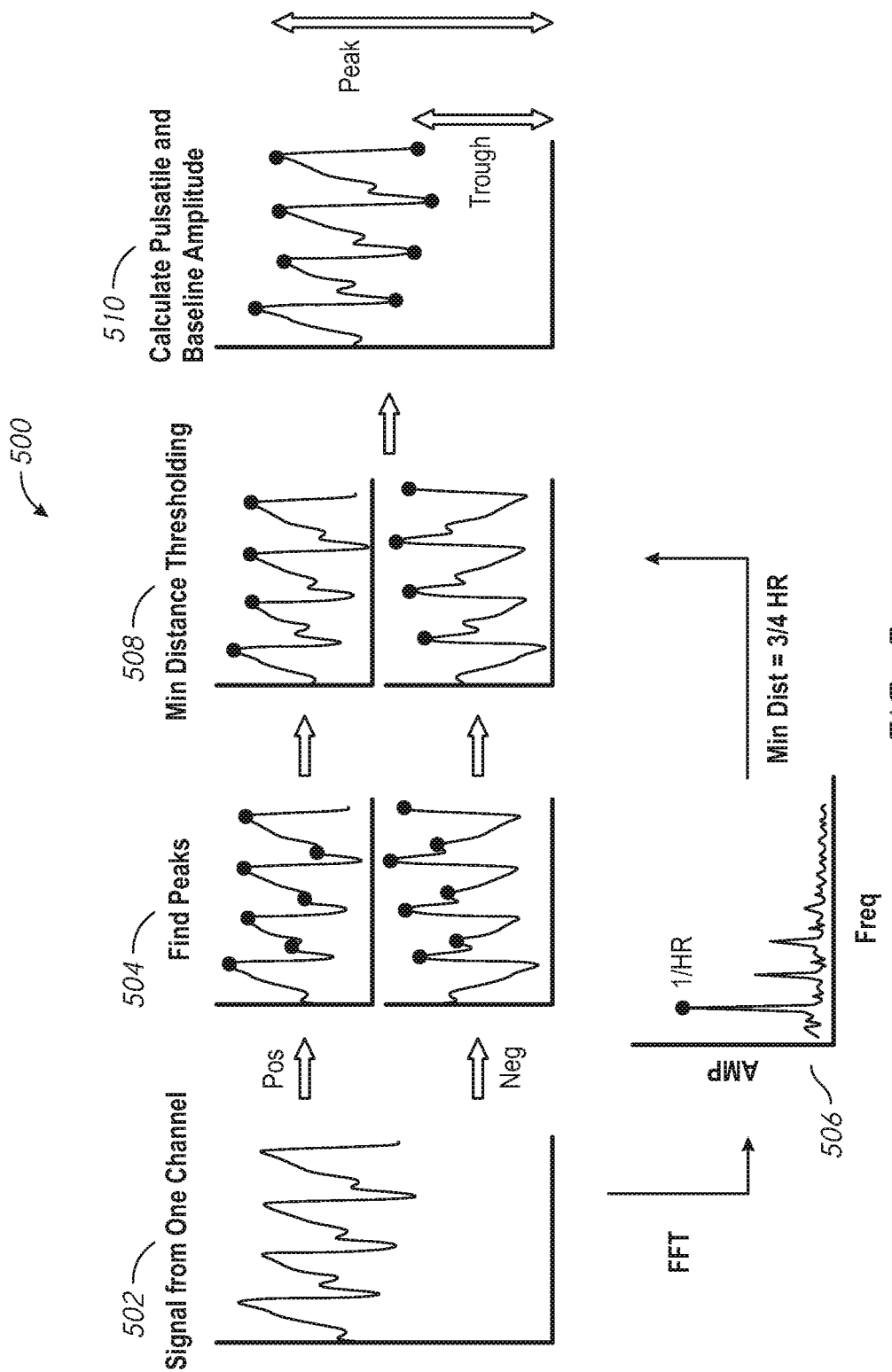
FIG. 5 is a schematic illustration of algorithms for processing video and/or image data arranged in accordance with examples described herein.

FIG. 5 is a schematic illustration of algorithms for processing video and/or image data arranged in accordance with examples described herein. For example, the algorithms and methodologies described with reference to FIG. 5 may be performed to extract features in phase 110 of FIG. 1. The electronic device 202 of FIG. 2 may be used to perform the algorithms and methods described with reference to FIG. 5. For example, the executable instructions for hemoglobin level prediction 212 may include instructions for performing the algorithms and methods described and depicted with reference to FIG. 5.

In phase 502, a signal from one channel may be obtained. The signal from the one channel may be time series data as described with reference to phase 108 in FIG. 1. For example, the signal in phase 502 may be an intensity signal from multiple frames of video data pertaining to a red channel responsive to illumination by a white LED. The frames of video data (and/or image data) may be processed to obtain the time series data. For example, only portions of captured frames may be used in some examples, such as a center section, in some examples measuring half the width and half the height of the image. Other portions may be used in other examples. Generally a portion of the video and/or image data which may demonstrate improved consistency and stability may be used (e.g. the center of a field of view in some examples). An improved stability area may be in other locations of the field of view in other examples, and may relate, for example, to locations in the field of view where the body part placed proximate the light source(s) and camera may experience a lesser degree of movement, or a location where there may be lesser interference from stray light sources in the environment.

In some examples video and/or image data obtained from a camera described herein may be filtered to provide the time series data in phase 502. For example, a high pass filter may be applied to remove fluctuations due to breathing. Breathing may be expected to have a frequency of around 0.2-0.3 Hz in some examples. Accordingly, a high pass filter of 0.5 Hz may be used to eliminate and/or reduce fluctuations due to breathing in some examples. Other filter thresholds may be used in other examples.

In some examples, an automated signal quality detector may be provided that may detect whether a signal is stable enough for analysis. For example, expected components in the signal include the pulse signal and the breathing signal, both of which are typically periodic between 0.3-2 Hz. An automated system may analyze for sudden DC shifts caused by the shifting of the body part, resulting in a non-periodic signal alteration. This signal quality detector may then determine whether a segment of collected data is useable for analysis, prompting the user to perform the data collection again if it failed.

Generally, the signal in phase 502 may be time series data related to a channel specific to particular wavelengths responsive to illumination by a particular light source or combination of light sources. Generally, the methodology depicted in FIG. 5 may be performed for each lighting condition and channel of interest.

In phase 504, the peaks of the filtered signal from phase 502 may be identified.

In phase 506, a dominant frequency in the signal from phase 502 may be identified. For example, a fast Fourier transform (FFT) may be performed on the filtered waveform from phase 502, and the dominant peak may be identified. The dominant peak may provide an estimate of the heart rate.

Using the heart rate identified in phase 506 as a threshold between successive peaks, unwanted peaks due, for example, to the dicrotic notch and the diastolic peak may be avoided and/or discarded. In some examples, the threshold may be set at a fraction (e.g. ¾) of the heart rate to avoid and/or reduce missing actual peaks. Accordingly, in phase 508, by enforcing a minimum distance between peaks, unwanted peaks may be discarded.

In phase 510, the peaks and troughs may be mapped onto the original signal (e.g. the signal from phase 502). The original magnitudes of the peaks and troughs may be used to calculate $I_R$. $I_R$ may be calculated based on a ratio of the peak to trough intensity. For example, $I_R$ may be given as the natural log of the ratio between the intensity of the peak and the intensity of the trough (e.g. $I_{peak}/I_{trough}$). $I_R$ may be calculated for each peak.

In order to estimate the absorption coefficients at the broadband wavelengths used in systems described herein, multiple features may be calculated based on the signals received across channels and lighting conditions. The first three features described below are derived directly from the Beer-Lambert equations in hemachrome analysis. The fourth and fifth features may aim to capture nonlinear interactions between wavelengths. Accordingly, features may be used associated with nonlinear interactions between channels (e.g. wavelengths).

A first feature, $I_{DC}$, may be equal to the intensity of a peak ($I_{peak}$) and may indicate a baseline intensity due to tissue.

A second feature, $I_{AC}$, may be equal to the difference between the peak and trough intensities (e.g. $I_{peak}-I_{trough}$). The feature $I_{AC}$ may accordingly represent an amplitude of pulsatile absorption.

A third feature, $I_R$ may, as discussed, be equal to the natural log of the ration between the peak and trough intensities for a given channel (e.g. wavelength). Accordingly, $I_R$ may be given as the ln ($I_{peak}/I_{trough}$).

A fourth feature, $I_{R,AC}$, for a pair of wavelengths, may provide a pairwise ratio of pulsatile absorptions between channels (e.g. wavelengths).

For example, $I_{R,AC}$ may be given as:

$$I_{R,AC}(\lambda_i,\lambda_k)=I_{AC,\lambda_i}/I_{AC,\lambda_k} \quad \text{Equation 5}$$

providing a ratio of pulsatile absorption between two different channels (e.g. two frequencies).

A fifth feature, $I_{R,ACDC}$, may provide an adjusted absorption difference between channels, (e.g. adjusted with a baseline).

For example, $I_{R,ACDC}$ may be given as:

$$I_{R,ACDC}(\lambda_i, \lambda_k) = \left| \frac{(I_{R,\lambda i} - I_{R,\lambda k})}{I_{DC,\lambda i} - I_{DC,\lambda k}} \right| \quad \text{Equation 6}$$

providing for an absolute value of a ratio between the difference between the $I_R$ features for two channels (e.g. channel i and k) and the difference between the baseline intensity $I_{DC}$ for the two channels.

In this manner, features may be extracted which reflect comparisons between multiple channels received by cameras described herein. This may assist in predicting hemoglobin levels when utilizing broadband light sources (e.g. white LEDs).

The features which may be extracted and/or used to predict hemoglobin levels may be based on the light source(s) and/or channels (e.g. optical sensors) used in the system. For example, for a given set of light source(s) that will be used to illuminate a body part, and a set of optical sensors sensitive to particular wavelengths, there may be a set of features which accurately correlate to the predicted hemoglobin level.

Generally, examples described herein utilize a model to correlate the predicted hemoglobin level to a set of features. The features may be compared to the model to predict the hemoglobin level. For example, a regression may be performed on the features to predict the hemoglobin level.

The model may be developed using a set of training data where hemoglobin levels for a population is obtained through blood tests. Data for the same population may be collected using systems described herein having a particular set of light source(s) and optical sensors sensitive to particular wavelengths. A regression may be performed on the data to both (1) select a set of features for use in predicting hemoglobin levels in future patients; and (2) develop a model for relating those selected features to predicted hemoglobin level.

The regression performed may be a linear regression and/or a SVM regression. In some examples, a linear regression may be performed on training data to select a set of features while an SVM regression may be used on patient data to predict hemoglobin levels.

Training performed using the three arrangements in FIG. 3 yielded a set of features which may be advantageously extracted in those arrangements to predict hemoglobin levels.

For example, in arrangement 302 of FIG. 3, in some examples, a white LED and a 970 nm LED may be used to implement the light sources. A collection of five features may be used to predict hemoglobin levels in the arrangement 302, as follows:

(1) an amplitude of pulsatile absorption (e.g. $I_{AC}$) of the image data from an optical sensor for a red channel (e.g. sensitive to the red wavelengths) responsive to illumination by the white light source, (2) an amplitude of pulsatile absorption (e.g. $I_{AC}$) of image data from an optical sensor for a blue channel (e.g. sensitive to the blue wavelengths) responsive to illumination by the white light source, (3) an amplitude of pulsatile absorption (e.g. $I_{AC}$) of image data from the optical sensor for a red channel (e.g. sensitive to the red wavelengths) responsive to illumination by the 970 nm light source, (4) a pairwise ratio of pulsatile absorptions (e.g. $I_{R,AC}$) between the image data from the optical sensor for the blue channel responsive to illumination by the white light source and the image data from the optical sensor for the red wavelengths responsive to illumination by the white light source; and (5) an adjusted absorption difference between channels (e.g. $I_{R,ACDC}$) between the image data from the optical sensor for the red channel responsive to illumination by the white light source and the image data from the optical sensor for the red wavelengths responsive to illumination by the 970 nm light source.

In arrangement 310 of FIG. 3 in some examples, a white LED, a 970 nm LED, and an incandescent bulb may be used to implement the light sources. A collection of six features may be used to predict hemoglobin levels in the arrangement 310, as follows:

(1) a pairwise ratio of pulsatile absorptions (e.g. $I_{R,AC}$) between the image data from the optical sensor for the red channel responsive to illumination by the incandescent light source and the image data from the optical sensor for the blue channel responsive to illumination by the white LED;

(2) a pairwise ratio of pulsatile absorptions (e.g. $I_{R,AC}$) between the image data from the optical sensor for the red channel responsive to illumination by the incandescent light source and the image data from the optical sensor for the red channel responsive to illumination by the 970 nm LED;

(3) a pairwise ratio of pulsatile absorptions (e.g. $I_{R,AC}$) between the image data from the optical sensor for the blue channel responsive to illumination by the incandescent light source and the image data from the optical sensor for the blue channel responsive to illumination by the white LED;

(4) an adjusted absorption difference between channels (e.g. $I_{R,ACDC}$) between the image data from the optical sensor for the red channel responsive to illumination by the incandescent light source and the image data and image data from the optical sensor for the blue channel responsive to illumination by the incandescent light source;

(5) an adjusted absorption difference between channels (e.g. $I_{R,ACDC}$) between the image data from the optical sensor for the red channel responsive to illumination by the incandescent light source and image data from the optical sensor for the blue channel responsive to illumination by the white LED; and (6) an adjusted absorption difference between channels (e.g. $I_{R,ACDC}$) between the image data from the optical sensor for the blue channel responsive to illumination by the white LED and image data from the optical sensor for the red channel responsive to illumination by the 970 nm light source.

In another arrangement in some examples, a white LED, a 970 nm LED, an 880 nm LED, and an incandescent light source may be used to implement the light sources. A collection of seven features may be used to predict hemoglobin levels in such an arrangement, as follows:

(1) a pairwise ratio of pulsatile absorptions (e.g. $I_{R,AC}$) between the image data from the optical sensor for the red channel responsive to illumination by the incandescent light source and the image data from the optical sensor for the red channel responsive to illumination by the 880 nm LED;

(2) a pairwise ratio of pulsatile absorptions (e.g. $I_{R,AC}$) between the image data from the optical sensor for the blue channel responsive to illumination by the incandescent light source and the image data from the optical sensor for the red channel responsive to illumination by the white LED;

(3) a pairwise ratio of pulsatile absorptions (e.g. $I_{R,AC}$) between the image data from the optical sensor for the red channel responsive to illumination by the white LED and the image data from the optical sensor for the blue channel responsive to illumination by the white LED:

(4) an adjusted absorption difference between channels (e.g. $I_{R,ACDC}$) between the image data from the optical sensor for the red channel responsive to illumination by the incandescent light source and the image data and image data from the optical sensor for the blue channel responsive to illumination by the incandescent light source;

(5) an adjusted absorption difference between channels (e.g. $I_{R,ACDC}$) between the image data from the optical sensor for the red channel responsive to illumination by the incandescent light source and image data from the optical sensor for the red channel responsive to illumination by the 970 nm LED; and (6) an adjusted absorption difference between channels (e.g. $I_{R,ACDC}$) between the image data from the optical sensor for the red channel responsive to illumination by the white LED and image data from the optical sensor for the red channel responsive to illumination by the 880 nm light source; and (7) an adjusted absorption difference between channels (e.g. $I_{R,ACDC}$) between the image data from the optical sensor for the blue channel responsive to illumination by the white LED and the image data from the optical sensor for the red channel responsive to illumination by the 880 nm light source.

The above are examples of selected features that may be used for predicting hemoglobin levels using particular light source and optical sensor pairs. Other features may be used in other examples. The features to be used may generally be selected using a regression and selecting a group features that are most indicative of hemoglobin level.

Predictions of hemoglobin levels described herein may be used in a variety of setting. For example, hemoglobin level may be used for screening anemia, and/or assessing a patient's response to iron supplement treatments.

Examples of hemoglobin level predictions described herein, which may be implemented in some examples on unmodified mobile phones, may have the advantage of being easily deployable and may enable previously unconsidered treatment management options. For example, devices and methods described herein may help users, such as community health workers in developing countries, screen for iron-deficient anemia caused by malnutrition. A major barrier for users may be the number of medical tools they need to transport with them on foot for each test. A smartphone is now standard equipment used for telemetry of records; as such, a smartphone-based solution may help reduce the burden on these workers and reduces the cost of equipment. Beyond improved deployability in remote areas, the reuse of smartphones may also aid people being treated for cases of anemia and need to monitor their condition at home. Often, these patients are treated with iron supplements and return to the hospital for a blood test every few weeks to ensure their treatment is effective. A smartphone hemoglobin test as described herein may be convenient for at-home monitoring and may not require a patient to purchase a specialized blood testing device that may cost hundreds to thousands of dollars. This may allow both the patient and the doctor to track the effectiveness of these treatments much more easily and frequently. This can help early detection of any ineffective treatment leading to complications.

The ability to measure hemoglobin noninvasively as described herein may be useful for measuring hemoglobin more frequently even in a clinical setting. For example, sickle cell patients often suffer from extreme anemia and need frequent monitoring. However, due to treatment to suppress their production of sickled cells, their veins are often hardened, making blood draw difficult.

Systems and methods described herein may accordingly find use as a malnutrition screening tool (e.g. based on whether a patient is anemic). Other example applications include determining a need for a blood transfusion (e.g. in the case of malaria patients), anemia monitoring, assisting in rehabilitation of leukemia patients (e.g. to predict if hemoglobin is high enough to exercise), and pregnancy monitoring for anemia.

EXAMPLE STUDY

A study was conducted with 31 patients. The study population included a wide spread of hemoglobin levels (8-16 g/dL), an age spread from 6 to 77 years old, and included skin tones ranging from pale to dark skin. The combination of incandescent and LEDs (e.g. arrangement 310 of FIG. 3) was found to give the best estimation accuracy of ±1.26 g/dL (R=0.82).

The IR LEDs used were sourced from the Marubeni SMC2 series. A Nexus 5 mobile phone with an unmodified front-facing camera was used.

Each lighting condition was shined continuously for 15 seconds and cycled to the next light with an assumption that hemoglobin concentration and average blood flow does not change significantly during the course of the test, which took a few minutes.

A mobile app was built on the Android platform with the Android Camera 2 API, which allows for full control over the white balancing and exposure. The full control was advantageous because infrared is generally considered an unwanted spectral response that camera applications may detect and rebalance settings to avoid. Certain white balancing settings, such as the "incandescent mode," can be used to avoid the rebalancing. The Camera 2 API allows for full control over the exposure, white balance, and sensor sensitivity. The hardware gains were manually set for each RGB channel using presets that are empirically found for each lighting condition such that the three channels reported a similar level of light. This was advantageous because the red channel typically has a much stronger response due to the red blood under the white and incandescent lights. If left to a flat white balance, the auto exposure may be set to the red channel, leaving the G and B channels highly underexposed in this example.

Exposure was set using the camera API's autoexposure settings. Once the image is auto-exposed, the exposure was locked and a 15-second video was recorded for each of the lighting conditions (e.g. each light source) sequentially. Each light source was cycled through one after another and a 15 second RGB video was recorded for each light source. The exposure, frame rate, white balance gain, and ISO settings were recorded for calibration. At an average resting heart rate of about 75 beats per minute (BPM), around 15-20 pulses were captured for each light source.

A separate SVM regression (SVR) model was trained for each of three embodiments using different light sources: (1) white+970 nm LED, (2) white+970 nm LED+incandescent light. (3) white+970 nm+880 nm LED+incandescent light. Each embodiment is referred to herein as EMB1, EMB2, and EMB3. The regressions were made based on ground truth values obtained from a blood test. During development, it was found that a linear regression did not produce as good of a result in these examples an SVR, but did provide good insight into feature significance. As such, the linear regression was used to help in the feature selection process, as it was easier to interpret the resultant model, but the SVR was used to produce a model for evaluation by employing the features chosen through the linear regression. Table 1 displays the feature list for the three embodiments:

TABLE 1

Features used for training in each embodiment.

| EMB1 | EMB2 | EMB3 |
|---|---|---|
| $I_{AC}$(WhR) | $I_{R,\,AC}$(InR, WhB) | $I_{R,\,AC}$(InR, 880) |
| $I_{AC}$(WhB) | $I_{R,\,AC}$(InR, 970) | $I_{R,\,AC}$(InB, WhR) |
| $I_{AC}$(970) | $I_{R,\,AC}$(InB, WhB) | $I_{R,\,AC}$(WhR, WhB) |
| $I_{R,\,AC}$(WhR, WhB) | $I_{R,\,ACDC}$(InR, InB) | $I_{R,\,ACDC}$(InR, InB) |
| $I_{R,\,ACDC}$(WhR, 970) | $I_{R,\,ACDC}$(InR, WhB) | $I_{R,\,ACDC}$(InR, 970) |
|  | $I_{R,\,ACDC}$(WhB, 970) | $I_{R,\,ACDC}$(WhR, 880) |
|  |  | $I_{R,\,ACDC}$(WhB, 880) |

In Table 1, the features used are listed, with the notations in the parenthetical being the light source and channel pair or pairs associated with the feature. For example, embodiment 1 (employing a white LED and a 970 nm LED) utilized:

$I_{AC}$ calculated from the red channel data responsive to illumination by the white LED.

$I_{AC}$ calculated from the blue channel data responsive to illumination by the white LED.

$I_{AC}$ calculated from the response (which would have been in the red channel) to illumination by the 970 nm LED.

$I_{R,AC}$ calculated from the red and blue channel responses to illumination by the white LED.

$I_{R,ACDC}$ calculated from the red channel response to illumination by the white LED and the red channel response to illumination by the 970 nm LED.

The features listed in Table 1 were found to provide an accurate map to predicted hemoglobin levels in accordance with modeled data.

The SVM model was tested using a leave-one-subject out validation. The training was done using the MATLAB implementation of SVM regression with a Gaussian kernel with default parameters, to avoid overfitting due to parameter tuning.

A study was conducted with three groups of people: healthy students and staff, in-patients at a children's cancer and transfusion clinic, and in-patients at an adult cancer and bone marrow transplant clinic. Data collections at these sites provided a diverse dataset paired with ground-truth hemoglobin concentration from CBC tests. The study included 31 patients in a range of 8.3 g/dL to 15.8 g/dL.

Each patient's data set included a series of videos measuring the absorption change under multiple wavelengths of light. Videos were collected using systems in accordance with examples described herein within 24 hours of the ground truth CBC blood draw to ensure that hemoglobin measures are as accurate as possible. Within a day, hemoglobin concentration is typically stable within 0.5 g/dL. Patients who have hemoglobin transfusion or heavy bleeding between the study and the blood draw were excluded.

In order to evaluate the effects of camera hardware and lighting conditions, we built a setup that allowed us to efficiently cycle through all the combinations for every subject in our validation. The setup used an acrylic box that contained a Bluetooth-enabled microcontroller that controlled each of the light sources. The top of the box had a 6 W incandescent light and a white piece of card stock with a hole cut in the middle. A Nexus 5 smartphone was placed in the box with the camera pointing up to the ceiling of the box. The LED circuit was then placed over the camera. The box was clear except for the portion holding the electronics, which let ambient light shine through. The box also had a black cover that was used to block out ambient light. Light sources that were used were the incandescent light, a white LED, a 970 nm LED and an 880 nm LED.

The subject placed the fingertip of the ring finger on their non-dominant hand on the camera. The subject was asked to sit still and not speak during the test to reduce movement. Each lighting condition was then cycled through in the following order: incandescent, white, 970 nm, 880 nm.

The study included taking a series of videos of the participant's finger under various lighting conditions. Tests were done during the day, with no particular control over the ambient lighting conditions. An optical hemoglobin measurement was also obtained using the FDA cleared Masimo Pronto 7 right before the recordings with the system described herein. The CBC blood test was used as ground-truth data and the optical Hb was used as a source of comparison to a specialized noninvasive device.

Hemoglobin predictions made in accordance with systems and methods described herein correlated with the CBC's predictions with a rank order correlation of 0.69, 0.74, and 0.82 with a mean error of 1.56 g/dL, 1.44 g/dL, and 1.26 g/dL respectively for each embodiment. The results of the Pronto were also compared to the CBC, which yielded a rank order correlation of 0.81 with a mean error of 1.28 g/dL. Generally, including incandescent light source improved correlation and decreased error. Use of an extra IR source (e.g. both the 970 nm and 880 nm sources) further improved performance.

From the foregoing it will be appreciated that, although specific embodiments of the invention have been described herein for purposes of illustration, various modifications may be made without deviating from the spirit and scope of the invention.

What is claimed is:

1. A device comprising:
   a plurality of light sources including at least one broadband light source configured to provide light in a range of wavelengths, the plurality of light sources positioned to illuminate a body part when placed in a target area;
   a camera including optical sensors, the camera positioned to receive reflected light from the body part when placed in the target area, the optical sensors configured to detect incident light having respective wavelengths within the range of wavelengths and provide image data for the respective wavelengths; and
   at least one processor and computer readable media encoded with instructions, including instructions which, when executed, cause the device to:
   extract features from the image data for the respective wavelengths, the features selected based on the plurality of light sources and the optical sensors, the features comprising at least a pairwise ratio of pulsatile absorptions between the image data from at least one optical sensor configured to detect blue wavelengths responsive to illumination by a white light source and the image data from at least another optical sensor configured to detect red wavelengths responsive to illumination by the white light source; and predict a hemoglobin level based on a comparison of the features to a model comprising hemoglobin levels.

2. The device of claim 1, wherein the optical sensors are configured to detect incident light having wavelengths of less than 1000 nm.

3. The device of claim 1, wherein the broadband light source comprises the white light source and the at least one optical sensor configured to detect red wavelengths and the at least another optical sensor configured to detect blue wavelengths.

4. The device of claim 3, wherein the plurality of light sources further include an infrared light source.

5. The device of claim 4 wherein the features comprise:

an amplitude of pulsatile absorption of the image data from the at least another optical sensor configured to detect red wavelengths responsive to illumination by the white light source;

an amplitude of pulsatile absorption of image data from the at least one optical sensor configured to detect blue wavelengths responsive to illumination by the white light source;

an amplitude of pulsatile absorption of image data from the optical sensor configured to detect blue wavelengths responsive to illumination by the infrared light source;

an adjusted absorption difference between the image data from the at least another optical sensor configured to detect red wavelengths responsive to illumination by the white light source and the image data from the optical sensor configured to detect blue wavelengths responsive to illumination by the infrared light source.

6. The device of claim 1, wherein the features include features associated with nonlinear interactions between wavelengths.

7. The device of claim 1, wherein the plurality of light sources include an incandescent light source.

8. The device of claim 1, wherein the device comprises a mobile phone.

9. The device of claim 1, wherein the computer readable media is further encoded with instructions which, when executed, cause the device to sequentially illuminate the target area with each of the plurality of light sources.

10. The device of claim 1, wherein the computer readable media is further encoded with instructions which, when executed, cause the device to provide an indication of a failed anemia screening when the hemoglobin level is below a threshold level.

11. The device of claim 1, wherein the features are selected using a regression for the plurality of light sources and the optical sensors based on blood test values.

12. The device of claim 11, wherein the regression is a linear regression or a support vector machine regression.

* * * * *